(12) United States Patent
Vijaykar et al.

(10) Patent No.: US 9,145,365 B2
(45) Date of Patent: Sep. 29, 2015

(54) PROCESS FOR THE PREPARATION OF ROFLUMILAST

(71) Applicant: MYLAN LABORATORIES LTD., Hyderabad (IN)

(72) Inventors: Priyesh Vijaykar, Hyderabad (IN); Dattatrey Kokane, Hyderabad (IN); Sushant Gharat, Hyderabad (IN); Dhananjay Shinde, Hyderabad (IN); Manojkumar Bindu, Hyderabad (IN); Vinayak Gore, Hyderabad (IN)

(73) Assignee: Mylan Laboratories Ltd., Jubilee Hills, Hyderabad (IN)

( * ) Notice: Subject to any disclaimer, the term of this patent is extended or adjusted under 35 U.S.C. 154(b) by 0 days.

(21) Appl. No.: 14/273,270

(22) Filed: May 8, 2014

(65) Prior Publication Data

US 2014/0275551 A1    Sep. 18, 2014

Related U.S. Application Data

(63) Continuation of application No. PCT/IN2012/000738, filed on Nov. 8, 2012.

(30) Foreign Application Priority Data

Nov. 9, 2011    (IN) .......................... 3840/CHE/2011

(51) Int. Cl.
*C07D 213/75* (2006.01)
*C07C 45/64* (2006.01)
*C07C 51/29* (2006.01)

(52) U.S. Cl.
CPC .............. *C07D 213/75* (2013.01); *C07C 45/64* (2013.01); *C07C 51/29* (2013.01); *C07C 2101/02* (2013.01)

(58) Field of Classification Search
CPC ...... C07D 213/75; C07C 45/64; C07C 51/29; C07C 2101/02
See application file for complete search history.

(56) References Cited

U.S. PATENT DOCUMENTS 6,448,274 B2 *    9/2002    Friesen et al. ................. 514/352
2009/0221586 A1    9/2009    Okada et al.

FOREIGN PATENT DOCUMENTS

| WO | 2004033430 A2 | 4/2004 |
| WO | 2005026095 A1 | 3/2005 |
| WO | 2012147098 A2 | 11/2012 |

OTHER PUBLICATIONS

International Search Report for PCT/IN2012/000738 dated Sep. 25, 2013.

* cited by examiner

*Primary Examiner* — D M Seaman
(74) *Attorney, Agent, or Firm* — Andreas Baltazis/Kramer Amado

(57) ABSTRACT

The present invention relates to an improved process for the preparation of Roflumilast. The present invention also relates to crystalline Form-I of Roflumilast.

9 Claims, 3 Drawing Sheets

PROCESS FOR THE PREPARATION OF ROFLUMILAST

CROSS-REFERENCE TO RELATED APPLICATIONS

This application is a continuation of parent International Application Number PCT/IN2012/000738, which was filed Nov. 8, 2012 and claims priority to Indian Patent Application Number 3840/CHE/2011, which was filed on Nov. 9, 2011. The entire disclosure of all of the prior applications is hereby incorporated by reference herein in their entirety.

FIELD OF THE INVENTION

The present invention relates to an improved process for the preparation of Roflumilast and novel crystalline Form-I of Roflumilast.

BACKGROUND OF THE INVENTION

Roflumilast, chemically known as 3-cyclopropylmethoxy-4-difluoromethoxy-N-[3,5-di-chloropyrid-4-yl]-benzamide of Formula-I is an PDE4-inhibitor.

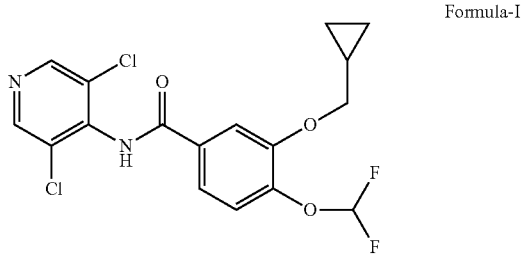 [SMILES: O=C(Nc1c(Cl)cncc1Cl)c1ccc(OC(F)F)c(OCC2CC2)c1]

Formula-I

Roflumilast is an effective phosphodiesterase-4-inhibitor (PDE4-inhibitor), which can be used in the treatment of asthma, inflammation, bronchitis, allergy, and osteoporosis, dermatoses and disorders related to immune system, heart and kidney.

Roflumilast is sold under the trademark Daliresp® and is available as an orally administered tablet. It is recommended at 500 mcg once daily.

U.S. Pat. No. 5,712,298 claims Roflumilast and its analogs. This patent also discloses a process for the preparation Roflumilast.

U.S. Pat. No. 6,448,274, PCT Publication No. WO 2005/026095. and PCT Publication No. WO 2004/033430 also disclose processes for the preparation of Roflumilast.

Polymorphism of Roflumilast is not reported in the literature.

One aspect of the present invention provides a stable and industrially scalable novel crystalline form of Roflumilast and an improved process for the preparation of Roflumilast.

SUMMARY OF THE INVENTION

One object of the present invention is to provide an improved process for the preparation of Roflumilast.

One aspect of the present invention provides an improved process for the preparation of Roflumilast comprising the steps of:

a) reacting 4-Difluoromethoxy-3-hydroxy benzaldehyde of Formula II with a cyclopropylmethyl compound of Formula III in the presence of an organic base to obtain 3-cyclopropylmethoxy-4-Difluoromethoxy benzaldehyde of Formula IV

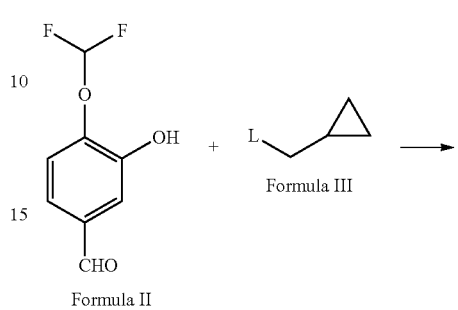

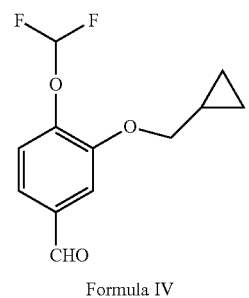

Formula IV wherein L is a leaving group selected from halogen, arylsulfonyloxy, alkylsulfonyloxy, b) oxidising the obtained aldehyde compound of Formula IV into 3-cyclopropylmethoxy-4-Difluoromethoxy benzoic acid of Formula V,

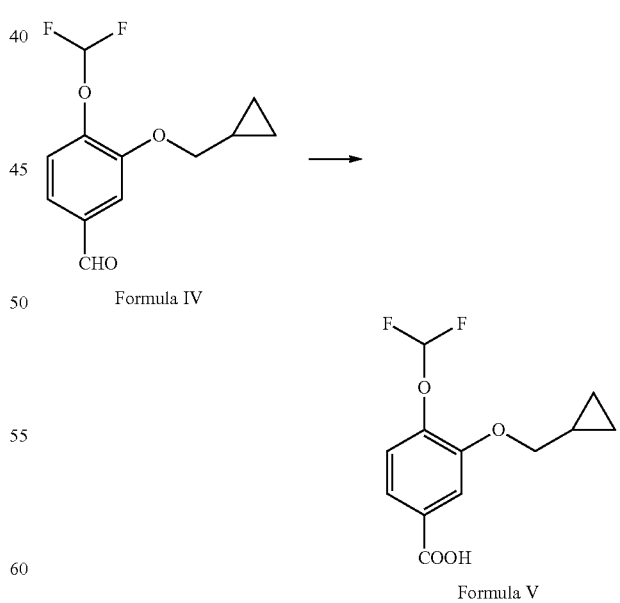

c) converting 3-cyclopropylmethoxy-4-Difluoromethoxy benzoic acid of Formula V to its acid halide and condensing with 4-amino-3,5 Dichloropyridine in presence of base to obtain Roflumilast, and

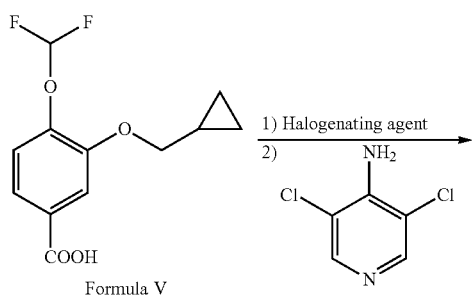

Formula V

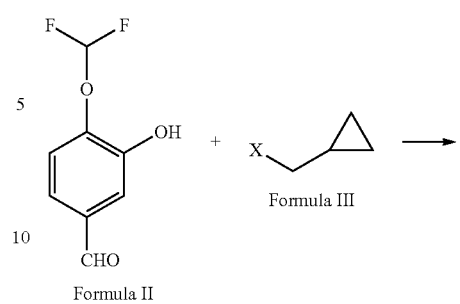

Formula II    Formula III

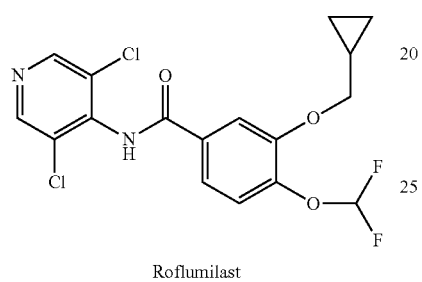

Roflumilast

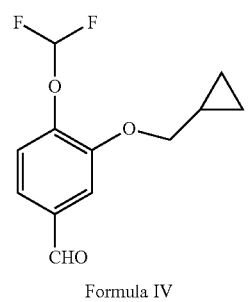

Formula IV d) optionally purifying Roflumilast in an organic solvent to get pure Roflumilast.

Another object of the present invention is to provide novel crystalline Form-I of Roflumilast and a process for the preparation of the same.

BRIEF DESCRIPTION OF THE DRAWINGS

Further objects of the present invention together with additional features contributing thereto and advantages accruing there from will be apparent from the following description of preferred embodiments of the invention which are shown in the accompanying drawing figures wherein.

DETAILED DESCRIPTION OF THE INVENTION

Figure 1:
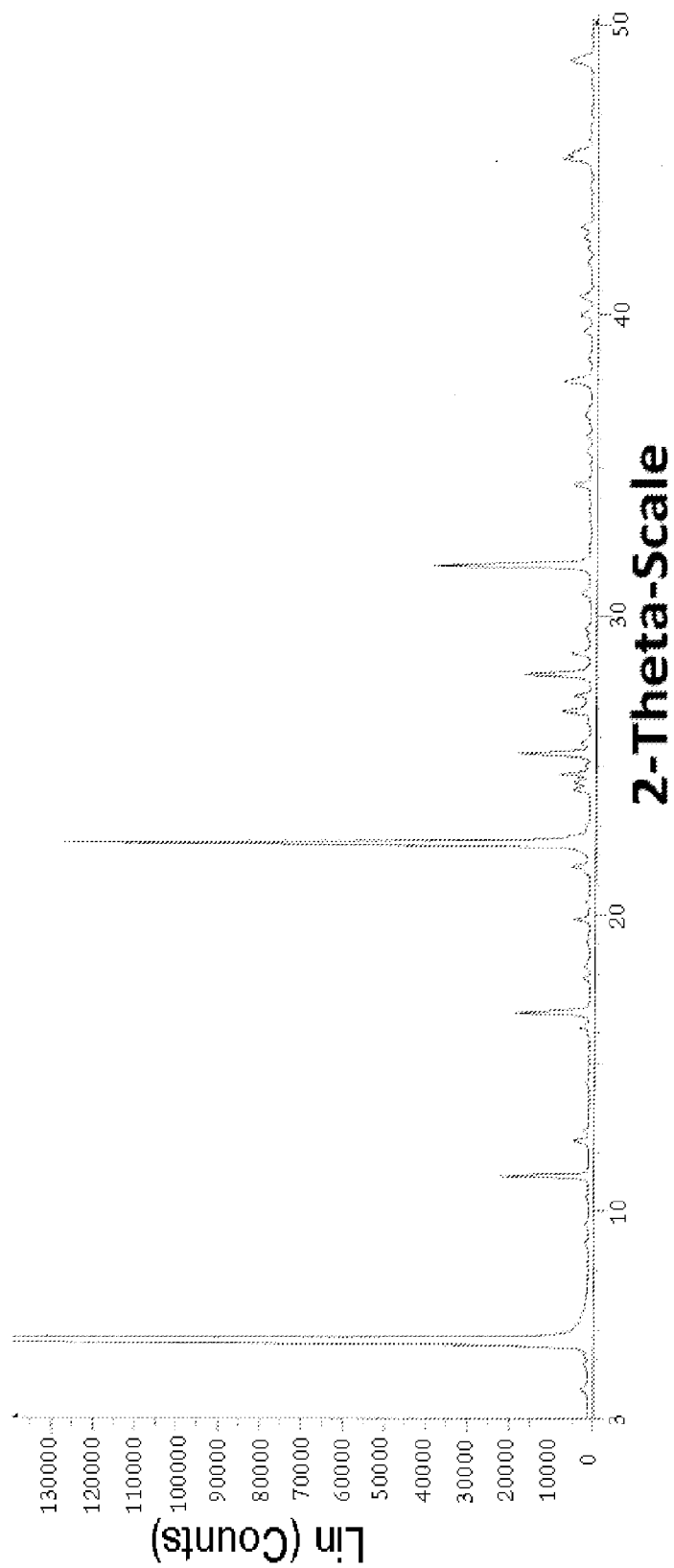
FIG. 1: illustrates the powder X-ray diffraction pattern of Roflumilast crystalline Form-I.

The present invention relates to an improved process for the preparation of Roflumilast and a novel polymorphic form of Roflumilast.

One aspect of the present invention is to provide an improved process for the preparation of Roflumilast comprising the steps of:

a) reacting 4-Difluoromethoxy-3-hydroxy benzaldehyde of Formula II with a cyclopropylmethyl compound of Formula III in the presence of an organic base to obtain 3-cyclopropylmethoxy-4-Difluoromethoxy benzaldehyde of Formula IV wherein X is a leaving group selected from halogen, arylsulfonyloxy, alkylsulfonyloxy, b) oxidising the obtained aldehyde compound of Formula IV into 3-cyclopropylmethoxy-4-Difluoromethoxy benzoic acid of Formula V;

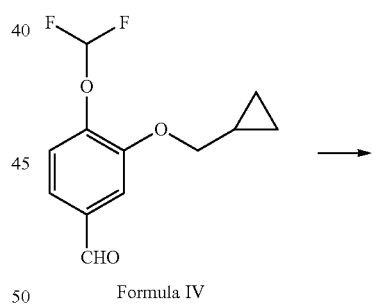

Formula IV

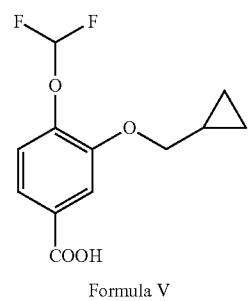

Formula V c) converting 3-cyclopropylmethoxy-4-Difluoromethoxy benzoic acid of Formula V to its acid halide and condensing with 4-amino-3,5 Dichloropyridine in presence of base to obtain Roflumilast; and

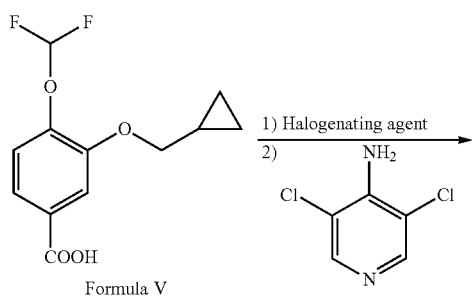

Formula V

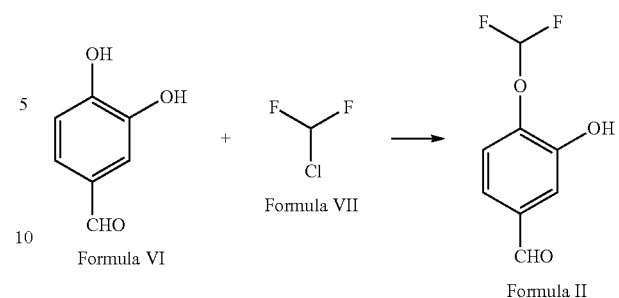

Formula VI + Formula VII → Formula II

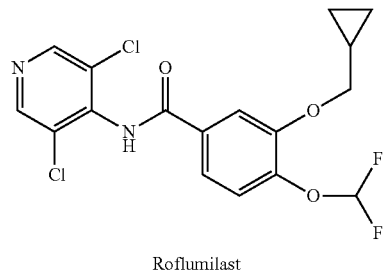

Roflumilast d) optionally purifying Roflumilast in an organic solvent to get pure Roflumilast.

In another embodiment, the organic base used in the step-a is selected from alkylamines such as triethylamine, disioproylethylamine; amidine compounds such as 1,8-Diazabicyclo[5.4.0]undec-7-ene (DBU), preferably 1,8-Diazabicyclo[5.4.0]undec-7-ene.

In one more embodiment, reaction of 4-Difluoromethoxy-3-hydroxy benzaldehyde with cyclopropylmethylhalide can be carried out using a phase transfer catalyst.

In one more embodiment, the leaving group used in step-a is selected from halogens such as F, Cl, Br and I; para-toluene sulfonate and methane sulfonate.

The compound of step-a (3-cyclopropylmethoxy-4-Difluoromethoxy benzaldehyde) obtained by reacting 4-Difluoromethoxy-3-hydroxy benzaldehyde with cyclopropylmethylhalide is isolated in mixture of EtOAc/water solvent system.

In another embodiment, oxidation of the aldehyde compound in step-b is carried out in presence of sulfamic acid and sodium chlorite.

In another embodiment, 3-cyclopropylmethoxy-4-Difluoromethoxy benzoic acid in step-c is converted into its acid halide by reacting with halogenating agents such as thionyl chloride or phosphorus oxychloride, preferably thionyl chloride.

In another embodiment, the base used in the step-c is selected from alkali metal hydrides or alkali metal carbonates. The alkali metal hydride used in this reaction is selected from sodium hydride and potassium hydride, preferably sodium hydride. The alkali metal carbonate used in this reaction is selected from sodium carbonate and potassium carbonate.

In another embodiment, the organic solvent used in step-d for the purification of Roflumilast is selected from alcoholic solvents such as methanol, ethanol and isopropanol.

In another embodiment, 4-Difluoromethoxy-3-hydroxy benzaldehyde of Formula II is prepared by reacting 3,4 Dihydroxybenzaldehyde of Formula VI with Difluorochloromethane of Formula VII in an organic solvent in presence of a base to obtain 4-Difluoromethoxy-3-hydroxy benzaldehyde, In this reaction the base is selected from potassium carbonate or sodium carbonate, preferably potassium carbonate, and the organic solvent is selected from N,N-Dimethylformamide, Dimethylacetamide or Dimethylsulfoxide, preferably N,N-Dimethylformamide.

Prior art procedures involve column purification of the 4-Difluoromethoxy-3-hydroxy benzaldehyde. Column purification is avoided in the present process, which results in a commercially feasible process with high yields. The compound 4-Difluoromethoxy-3-hydroxy benzaldehyde obtained by the condensation of 3,4 Dihydroxybenzaldehyde with Difluorochloromethane is isolated in a mixture of EtOAc (Ethyl acetate)/Heptane solvent system by avoiding the column purification.

Another aspect of the present invention is to provide novel crystalline Form-I of Roflumilast and a process for the preparation of the same.

Instrumentation

Powder X-Ray Diffraction (PXRD)

The said polymorphs of the present invention are characterized by their X-ray powder diffraction pattern. Thus, the X-ray diffraction patterns of said polymorphs of the invention were measured on PANalytical, X'Pert PRO powder diffractometer equipped with goniometer of θ/θ configuration and X'Celerator detector. The Cu-anode X-ray tube was operated at 40 kV and 30 mA. The experiments were conducted over the 2θ range of 2.0°-50.0°, 0.030° step size and 50 seconds step time.

Differential Scanning Calorimetry (DSC)

The DSC measurements were carried out on TA Q1000 of TA instruments. The experiments were performed at a heating rate of 10.0° C./min over a temperature range of 30° C.-300° C. purging with nitrogen at a flow rate of 50 ml/min. Standard aluminum crucibles covered by lids with three pin holes were used.

Thermogravimetric Analysis (TGA)

TGA was recorded on out using the instrument Mettler Toledo TGA/SDTA 851$^e$ and TGA Q5000 of TA instruments. The experiments were performed at a heating rate of 10.0° C./min over a temperature range of 30° C.-300° C. purging with nitrogen at a flow rate of 25 ml/min.

The present invention provides novel crystalline Form-I of Roflumilast.

In one embodiment, crystalline Form-I of Roflumilast is characterized by X-ray powder diffraction having a characteristic peak at 5.59±0.2°2θ.

In another embodiment, crystalline Form-I of Roflumilast is characterized by X-ray powder diffraction having characteristic peaks at 5.59 and 22.4±0.2°2θ.

In another embodiment, crystalline Form-I of Roflumilast is characterized by the Powder X-ray diffraction as depicted in FIG. 1.

Figure 2:
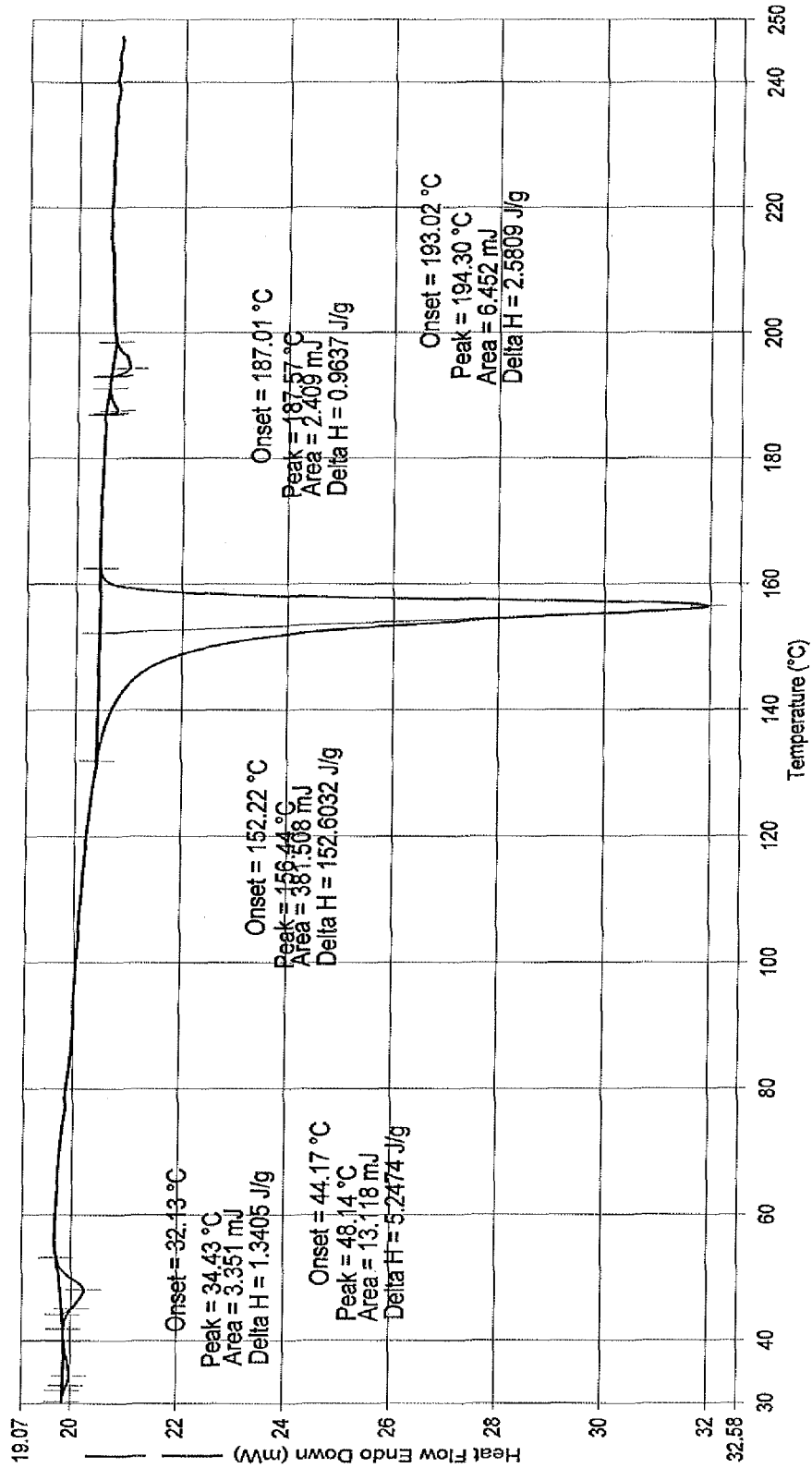
FIG. 2: illustrates DSC thermogram of Roflumilast crystalline Form-I.

In one more embodiment, crystalline Form-I of Roflumilast is characterized by the DSC thermogram as depicted in FIG. 2.

Figure 3:
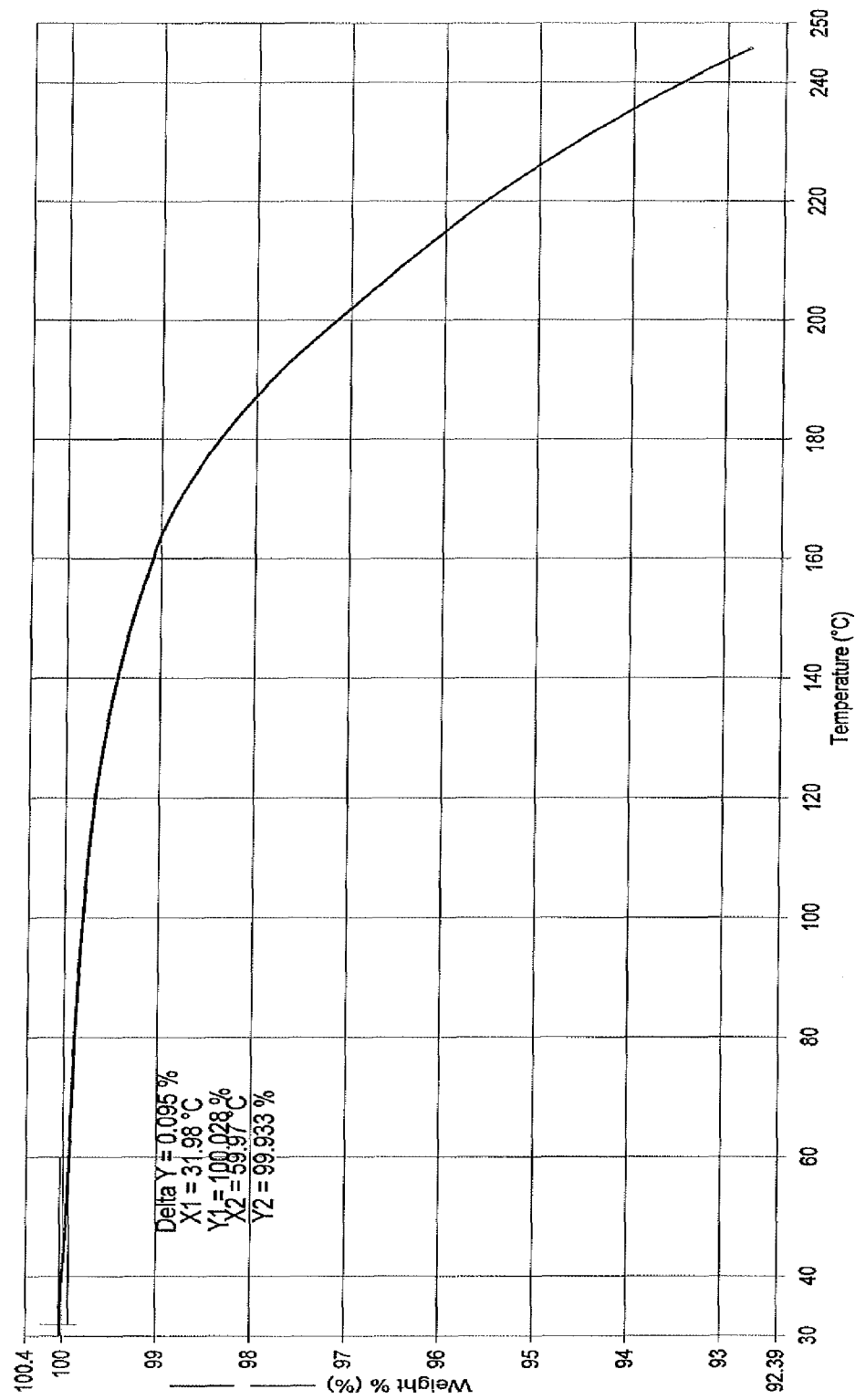
FIG. 3: illustrates TGA of Roflumilast crystalline Form-I.

In another embodiment, crystalline Form-I of Roflumilast is characterized by the TGA as depicted in FIG. 3.

Another aspect of the present invention provides process for the preparation of crystalline Form-I of Roflumilast comprising crystallization of Roflumilast in an organic solvent.

In one embodiment the organic solvents used for the crystallization of Roflumilast are selected from methanol, ethylacetate, isopropanol, n-heptane or mixtures thereof.

The invention is illustrated with the following examples, which are provided by way of illustration only and should not be construed to limit the scope of the invention.

EXPERIMENTAL PROCEDURE

Example-1

Process for the Preparation of 4-Difluoromethoxy-3-Hydroxy Benzaldehyde

A mixture of N,N-Dimethylformamide (5 vol. with respect to 3,4 Dihydroxybenzaldehyde) and potassium carbonate (1.2 eq respect to 3,4 Dihydroxybenzaldehyde) was taken in a vessel at 20-25° C. To this 3,4 Dihydroxybenzaldehyde was added and stirred for 10 min. The reaction mixture was heated to 80-85° C. Difluorochloromethane gas was purged for 8-10 hours. After completion of reaction, the reaction mixture was cooled to 25-30° C. Potassium carbonate was filtered off and washed with N,N Dimethylformamide. Water was added to the filtrate slowly and extracted with EtOAc. EtOAc extracts were washed with aq. HCl and water. EtOAc was distilled under vacuum, 100-10 mbar at 45-50° C. to get a thick oil. The oil was taken in toluene and water and stirred for 10-15 min. To this potassium carbonate in water was added and stirred for 1 hour. Layers were separated and toluene layer was again washed with water for 10-15 min. To this 10% (W/V) potassium carbonate in water was added and stirred for 1 hour. Layers were separated and the combined aq. layer was washed with toluene. Aq layer was cooled to 5-10° C., acidified with acetic acid, and stirred for 1 hour at 20-25° C. The solid was filtered and dried under vacuum at 45-50° C. The above solid was taken in 10% EtOAc/Heptane mixture and heated to reflux for 30 min. The slurry was filtered and the filtrate was concentrated under vacuum to get 4-Difluoromethoxy 3-hydroxy benzaldehyde.

Example-2

Alternative Process for the Preparation of 4-Difluoromethoxy-3-Hydroxy Benzaldehyde A mixture of N,N-Dimethylformamide (5 vol. with respect to 3,4 Dihydroxybenzaldehyde) and potassium carbonate (1.2 eq respect to 3,4 Dihydroxybenzaldehyde) was taken in a vessel at 20-25° C. To this 3,4 Dihydroxybenzaldehyde was added and stirred for 10 min. The reaction mixture was heated to 80-85° C. Difluorochloromethane gas was purged for 8-10 hours. After completion of the reaction, the reaction mixture was cooled to 25-30° C. Potassium carbonate was filtered off and washed with N,N Dimethylformamide. Water was added to the filtrate slowly and extracted with EtOAc. EtOAc extracts were washed with aq. HCl and water. EtOAc was distilled under vacuum, 100-10 mbar at 45-50° C. to get a thick oil. The oil was taken in toluene and water and stirred for 10-15 min. To this potassium carbonate in water was added and stirred for 1 hour. Layers were separated and the combined aq. layer was washed with toluene. Aq. layer was cooled to 5-10° C., acidified with acetic acid, and stirred for 1 hour at 20-25° C. The solid was taken in 10% EtOAc/Heptane mixture and heated to 79-82° C. for 15 min. Slurry was filtered and silica gel was added to filtrate and heated to 79-82° C. for 15 min. The slurry was filtered and concentrated under vacuum at 55-60° C. to get a solid. The solid was taken in n-Heptane and stirred for 30 minutes at 5-10° C. The solid was concentrated under vacuum to get 4-Difluoromethoxy 3-hydroxy benzaldehyde.

Example-3

Process for the Preparation of 3-Cyclopropylmethoxy-4-Difluoromethoxy Benzaldehyde 4-Difluoromethoxy 3-hydroxy benzaldehyde in tetrahydrofuran (5 vol with respect to 4-Difluoromethoxy 3-hydroxy benzaldehyde) was taken in a vessel and DBU (1.5 eq respect to 4-Difluoromethoxy 3-hydroxy benzaldehyde) was added. To this first lot of cyclopropylmethylbromide (1.5 eq respect to 4-Difluoromethoxy 3-hydroxy benzaldehyde) was added and heated to 75-80° C. After 2 hours second lot of cyclopropylmethyl bromide (0.5 eq with respect to 4-Difluoromethoxy 3-hydroxy benzaldehyde) was added and maintained at 75-80° C. for 2 hours. To this third lot of cyclopropylmethyl bromide (0.5 eq with respect to 4-Difluoromethoxy 3-hydroxy benzaldehyde) was added and maintained for 2 hours. The reaction mass was cooled to 20-25° C. and water was added. The reaction mixture was extracted with EtOAc and EtOAc extracts were washed with water. EtOAc was distilled out under reduced pressure at 40° C. to get 3-cyclopropylmethoxy 4-Difluoromethoxy benzaldehyde as brown oil.

Example-4

Process for the Preparation of 3-Cyclopropylmethoxy-4-Difluoromethoxy Benzoic Acid Glacial acetic acid (5 vol. with respect to 3-cyclopropylmethoxy 4-Difluoromethoxy benzaldehyde) was taken in a vessel and to this mixture of 3-cyclopropylmethoxy 4-Difluoromethoxy benzaldehyde and sulfamic acid (1.35 eq with respect to 3-cyclopropylmethoxy 4-Difluoromethoxy benzaldehyde) was added. The reaction mass was cooled to 5-10° C. under stirring. In another clean reaction vessel sodium chlorite (1.63 eq) was taken in water (1.5 vol. with respect to 3-cyclopropylmethyl 4-Difluoromethoxy benzaldehyde) and added dropwise to the above prepared reaction solution at temperature below 10° C. The reaction mixture was stirred for 1 hr at 5-10° C. After completion of the reaction, water was added to get a white slurry. The solid was filtered and washed with water and dried under vacuum at 45-50° C. to get 3-cyclopropylmethoxy 4-Difluoromethoxy benzoic acid.

Example-5

Process for the Preparation of Crude Roflumilast

In a clean reaction vessel, tetrahydrofuran (5 vol. with respect to 3-cyclopropylmethoxy 4-Difluoromethoxy benzoic acid) was taken and to this 3-cyclopropylmethoxy 4-Difluoromethoxy benzoic acid (1 eq) was added under stirring to get a clear solution. To this thionyl chloride (1.5 eq with respect to 3-cyclopropylmethoxy 4-Difluoromethoxy benzoic acid) was added drop wise at 20-25° C. and stirred for 30 min at 40-45° C. Thionyl chloride was distilled out at 40-45° C. to get an oil. This was swapped with tetrahydrofuran. In another flask sodium hydride (2.4 eq with respect to 3-cyclopropylmethoxy 4-Difluoromethoxy benzoic acid) was taken in THF (5 vol. with respect to 3-cyclopropylmethoxy 4-Difluoromethoxy benzoic acid). To this 4-amino 3,5 Dichloropyridine (1.2 eq with respect to 3-cyclopropylmethoxy 4-Difluoromethoxy benzoic acid) was added and stirred for 30 minutes. The above obtained acid chloride was dissolved in tetrahydrofuran (5 vol. with respect to 3-cyclopropylmethoxy 4-Difluoromethoxy benzoic acid) and added dropwise to the above prepared mixture of 4-amino 3,5 Dichloropyridine and sodium hydride at a temperature below 30° C. The above reaction mixture was stirred for 1 hr at 20-25° C. To this EtOAc was added followed by the addition of water. EtOAc layer was separated and the aqueous layer was extracted with EtOAc. Combined EtOAc layer was washed with 10% HCl and then with 10% aq. NaOH solution. This was washed with water and ethyl acetate and distilled out at 45 50° C. to get a light yellow colored solid. To this isopropanol was added and heated to reflux until a clear solution was obtained. The solution was cooled to 20-25° C. slowly and maintained at 20-25° C. for 1 hour. The solid was filtered and washed with isopropanol to get crude Roflumilast.

Example-6

Purification of Roflumilast

Roflumilast obtained in example 4 (1 eq) and isopropanol (5 vol with respect to Roflumilast) was refluxed to get a clear solution. The reaction mass was cooled to 20-25° C. and maintained at 20-25° C. for 1 hour. The solid was washed with isopropanol and dried under vacuum at 50° C. to get Roflumilast.

Example-7

Process for the Preparation of Form-I

Roflumilast (1 Eq) in indicated solvents at the indicated volumes was refluxed to get a clear solution. The reaction mass was cooled to 20-25° C. and maintained at 20-25° C. for 1 hour and the obtained solid was filtered and identified as Form-I.

| Input Material | Solvent (s) | volume |
| --- | --- | --- |
| Roflumilast | Methanol | 10 |
| Roflumilast | EtOAc | 10 |
| Roflumilast | Isopropanol:n-Heptane | 5/5 |

We claim:
1. A process for the preparation of Roflumilast comprising the steps of:
   a) reacting 4-Difluoromethoxy-3-hydroxy benzaldehyde of Formula II with a cyclopropylmethyl compound of Formula III in the presence of an organic base to obtain 3-cyclopropylmethoxy-4-Difluoromethoxy benzaldehyde of Formula IV

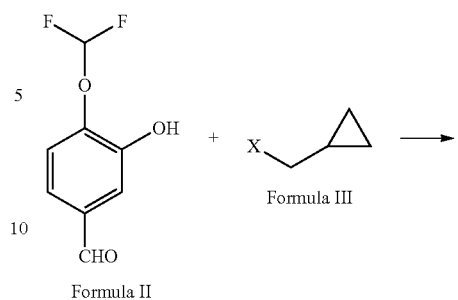

Formula II

Formula III

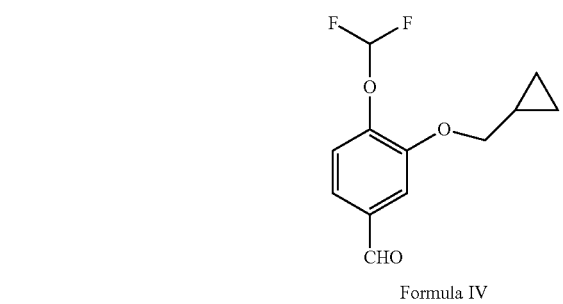

Formula IV wherein X is a leaving group, b) oxidising the obtained aldehyde compound of Formula IV into 3-cyclopropylmethoxy-4-Difluoromethoxy benzoic acid of Formula V,

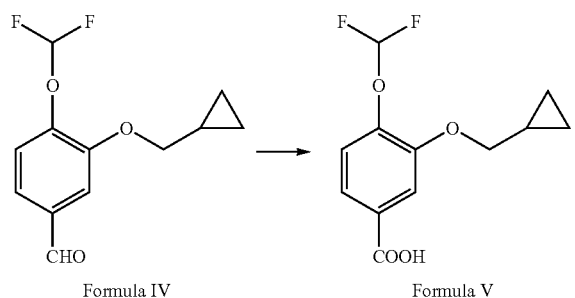 [SMILES: O=Cc1ccc(OC(F)F)c(OCC2CC2)c1 ; O=C(O)c1ccc(OC(F)F)c(OCC2CC2)c1]

Formula IV

Formula V c) converting 3-cyclopropylmethoxy-4-Difluoromethoxy benzoic acid of Formula V to its acid halide and condensing with 4-amino 3,5-Dichloropyridine in the presence of base to obtain Roflumilast, and

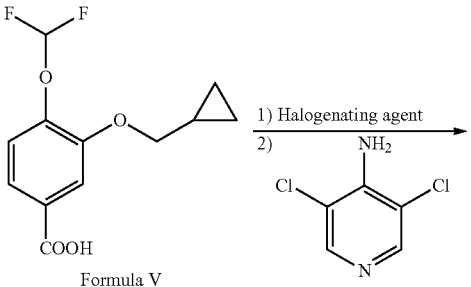

Formula V

-continued

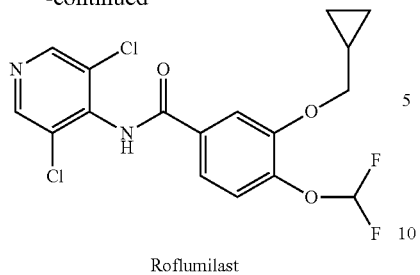

Roflumilast d) optionally purifying Roflumilast in an organic solvent to get pure Roflumilast.

2. The process according to claim 1, wherein the organic base used in the step-a is 1,8-Diazabicyclo[5.4.0]undec-7-ene (DBU).

3. The process according to claim 1, wherein the leaving group in step-a is selected from the group consisting of a halogen, alkylsulfonyloxy, and arylsulfonyloxy.

4. The process according to claim 1, wherein the oxidation in step-b is carried out in the presence of sulfamic acid and sodium chlorite.

5. The process according to claim 1, wherein the base used in the step-c is selected from the group consisting of alkali metal hydrides and alkali metal carbonates.

6. The process according to claim 5, wherein the base is selected from the group consisting of sodium hydride and potassium hydride.

7. The process according to claim 1, wherein the acid halide in step-c is produced using a halogenating agent and wherein the halogenating agent is thionyl chloride.

8. The process according to claim 1, wherein the organic solvent used in step-d for the purification of Roflumilast is selected from alcoholic solvents.

9. The process according to claim 8, wherein the alcoholic solvent is selected from the group consisting of methanol, ethanol, isopropanol, and mixtures thereof.

* * * * *